United States Patent
Dhanasingh et al.

(10) Patent No.: US 9,522,268 B2
(45) Date of Patent: Dec. 20, 2016

(54) MODIFIED ELECTRODE LEAD FOR COCHLEAR IMPLANTS

(71) Applicant: MED-EL Elektromedizinische Geraete GmbH, Innsbruck (AT)

(72) Inventors: Anandhan Dhanasingh, Innsbruck (AT); Claude Jolly, Innsbruck (AT); Anup Ramachandran, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/874,510

(22) Filed: Oct. 5, 2015

(65) Prior Publication Data

US 2016/0096012 A1     Apr. 7, 2016

Related U.S. Application Data

(60) Provisional application No. 62/060,065, filed on Oct. 6, 2014.

(51) Int. Cl.
*A61N 1/00* (2006.01)
*A61N 1/05* (2006.01)

(52) U.S. Cl.
CPC .................... *A61N 1/0541* (2013.01)

(58) Field of Classification Search
CPC .................................... A61N 1/0541
See application file for complete search history.

(56) References Cited

U.S. PATENT DOCUMENTS

| | | | |
|---|---|---|---|
| 6,421,569 B1 | 7/2002 | Treaba et al. | |
| 7,792,587 B2 | 9/2010 | Schmidt et al. | |
| 8,594,799 B2 | 11/2013 | Haller et al. | |
| 8,630,721 B2 | 1/2014 | Gantz | |
| 8,774,944 B2 | 7/2014 | Thenuwara et al. | |
| 2004/0127968 A1 | 7/2004 | Kuzma et al. | |
| 2015/0157852 A1* | 6/2015 | Jolly | A61N 1/0541 607/137 |
| 2015/0224300 A1 | 8/2015 | Hagr et al. | |

OTHER PUBLICATIONS

International Searching Authority, Authorized Officer Blaine R. Copenheaver, International Search Report and Written Opinion, PCT/US2015/053912, date of mailing Dec. 28, 2015.

* cited by examiner

*Primary Examiner* — Robert N Wieland
(74) *Attorney, Agent, or Firm* — Sunstein Kann Murphy & Timbers LLP

(57) ABSTRACT

An implantable electrode arrangement for a cochlear implant system is described. The arrangement includes a flexible intracochlear electrode array having an outer surface with electrode contacts for applying cochlear stimulation signals to target neural tissue within the implanted cochlea. A flexible extracochlear electrode lead is coupled at a lead proximal end to an implanted signal processor that provides the cochlear stimulation signals, and connected at a lead distal end to a proximal end of the electrode array. A lead holder is connected to the lead distal end and has an initial shape. The lead holder is malleable and adapted to be intra-surgically deformed into and retain a new desired shape so as to secure the lead distal end at the electrode opening into the implanted cochlea and decouple post-surgical mechanical strain at the lead distal end from the electrode array.

9 Claims, 10 Drawing Sheets

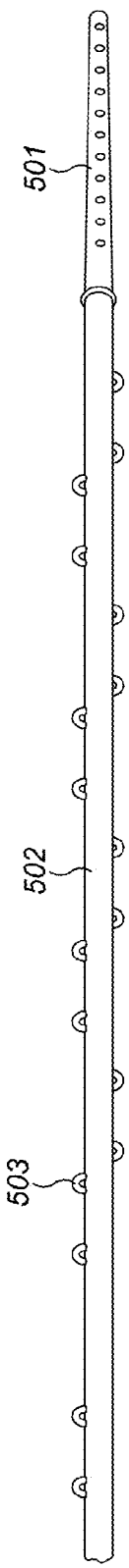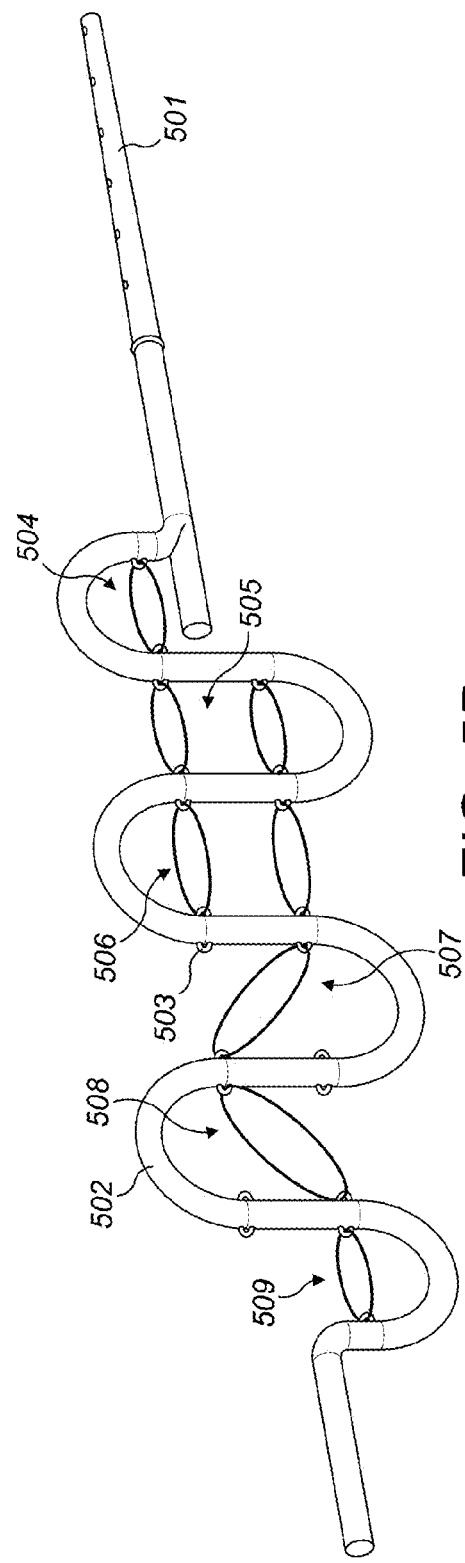
FIG. 5A
FIG. 5B

MODIFIED ELECTRODE LEAD FOR COCHLEAR IMPLANTS

This application claims priority from U.S. Provisional Patent Application 62/060,065, filed Oct. 6, 2014, which is incorporated herein by reference in its entirety.

TECHNICAL FIELD

The present invention relates to medical implants, and more specifically to an implantable electrode arrangement for cochlear implant systems.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by an auditory prosthesis system such as a cochlear implant that electrically stimulates auditory nerve tissue with small currents delivered by multiple electrode contacts distributed along an implant electrode. FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission into a receiver processor in an implant housing 108. Besides extracting the audio information, the receiver processor in the implant housing 108 may perform additional signal processing such as error correction, pulse formation, etc., and produces a stimulation pattern (based on the extracted audio information) that is sent through an electrode lead 109 to an implanted electrode array 110 which penetrates into the cochlea 104 through a surgical opening in the outer surface of the cochlea 104. Typically, this electrode array 110 includes multiple electrode contacts 112 on its surface that deliver the stimulation signals to adjacent neural tissue of the cochlea 104 which the brain of the patient interprets as sound. The individual electrode contacts 112 may be activated sequentially, or simultaneously in one or more contact groups.

Following implantation surgery, the mastoid bone continues to grow considerably in children. One recent article reported that the size of the mastoid bone expands 0.6-0.9 cm in length and 0.4 cm in width in the first year, followed by half again the growth until the age of 6-7 years, and thereafter slower growth until reaching adult size. The mastoid cells are about 3-5 $cm^2$ at one year old, followed by a linear growth till the age of 6 (1-1.2 $cm^2$/year) leading to an adult size of 12 $cm^2$. This growth in the mastoid bone and its air cells is important to consider when implanting children with cochlear implant systems. As the mastoid bone of the implanted patient grows over time, the electrode lead should be long enough to compensate for that growth so that the electrode array is not pulled out of the cochlea.

FIG. 2A shows structural details of a cochlear implant electrode arrangement at the electrode opening 201 into the implanted cochlea 104. Immediately after the insertion procedure, the electrode array 110 tends to lie toward the outer lateral wall of the spiral-shaped cochlea 104. Over time, growth of the mastoid bone can tend to pull back on the electrode lead 109 to retract the electrode array 110 back out through the electrode opening 201, as shown in FIG. 2B. Such post-surgical electrode retraction pulls the nearest electrode contact 112 away from its intended target neural tissue within the cochlea 104 back toward the electrode opening 201, or even further, back outside the cochlea 104 into the middle ear 104. This can produce pain sensation in the patient when that electrode contact 112 is energized. Usually in such circumstances, that electrode contact 112 will be inactivated and fewer electrode contacts 112 remain for use to produce sound sensation.

The degree of pull back varies depending on how deeply the electrode array 110 is inserted into the cochlea 104, how well the electrode lead 109 is looped in the mastoid opening, how well the electrode opening 201 is packed with fascia material, and the specific geometry at the electrode opening 201. Currently when the electrode lead 109 is longer than required (typically the case for small children), then it is looped in the mastoid opening so that it can compensate the growth of the mastoid bone. The looping of the electrode lead 109 differs from surgeon to surgeon and also varies with the patient's specific anatomy. There is no one standard looping procedure. In addition, excess slack in the electrode lead 109 that unloops out of the mastoid bowl due to growth of the mastoid bone can press against the overlying skin, which can be uncomfortable and cosmetically unsightly.

Various approaches have been attempted to resist such post-surgical lead retraction. A cork-shaped stopper has been used to tightly wedge the electrode lead in the electrode opening. An anti-retraction skirt has been implemented on the electrode array at the electrode opening which is made of polymer material that swells when contacted by the liquid preilymph medium, thereby holding the electrode array in place. The electrode lead has been mechanically clipped to the bony bridge to decouple the electrode array from mechanical forces on the electrode lead. Other electrode arrangements contain an internal malleable material on either side of the electrode opening which maintains a bent shape after full insertion of the electrode array to resist retraction. A surgical group in Hannover Germany has added to the implant electrode a wing of flexible silicone material that can be fixed to a groove in the bony material on the outer surface of the cochlea near the electrode opening. All of these efforts have suffered from various issues that leave each an imperfect solution.

SUMMARY

Embodiments of the present invention are directed to an implantable electrode arrangement for a cochlear implant system. The arrangement includes a flexible intracochlear electrode array having an outer surface with electrode contacts for applying cochlear stimulation signals to target neural tissue within the implanted cochlea. A flexible extracochlear electrode lead is coupled at a lead proximal end to an implanted signal processor that provides the cochlear stimulation signals, and connected at a lead distal end to a proximal end of the electrode array. A lead holder is connected to the lead distal end and has an initial shape. The lead holder is malleable and adapted to be intra-surgically deformed into and retain a new desired shape so as to secure the lead distal end at the electrode opening into the implanted cochlea and decouple post-surgical mechanical strain at the lead distal end from the electrode array. For example, the lead holder may include an embedded nitinol element with malleable characteristics.

In some specific embodiments, the lead holder may be in line with the electrode array and the electrode lead extends out from the lead holder at an angle, for example, a perpendicular angle. In such embodiments, there may be a sharp bend after the perpendicular angle so that the electrode lead extends substantially parallel to the electrode array. Or the electrode lead may be in line with the electrode array and the lead holder extends out from the lead distal end at an angle.

Embodiments of the present invention also include an implantable electrode arrangement for a cochlear implant system that includes a flexible intracochlear electrode array having an outer surface with electrode contacts for applying cochlear stimulation signals to target neural tissue within the implanted cochlea. A flexible extracochlear electrode lead is coupled at a lead proximal end coupled to an implanted signal processor that provides the cochlear stimulation signals, and connected at a lead distal end to a proximal end of the electrode array. The outer surface of the electrode lead has string connectors distributed thereon, and at least one connecting string attached at each end to a string connector to form a string connection that holds together a loop of the electrode lead between the attached string connectors. The loop is longer than the string connection, and the string connection is adapted to be removed after healing of the implanted cochlea following insertion of the electrode array to thereby decouple post-surgical mechanical strain on the electrode lead from the electrode array.

In further specific embodiments, the string connectors may be connector rings protruding from the outer surface, or connector loops attached to the outer surface. The string connection may be adapted to be removed by biodegrading over time of the connecting string or the attached string connectors, or by surgical cutting of the connecting string or the attached string connectors.

The electrode arrangement according also may include a lead handling member projecting out from the electrode lead without conducting elements that carry the cochlear stimulation signals. The lead handling member may include an embedded malleable core having an initial shape adapted to be intra-surgically deformed into and retain a new desired shape. For example, the embedded malleable core may include a nitinol element with malleable characteristics.

Embodiments of the present invention also include a cochlear implant system having an electrode arrangement according to any of the foregoing.

BRIEF DESCRIPTION OF THE DRAWINGS

FIGS. 5A-5D an electrode arrangement according to an embodiment of the present invention with connecting strings.

DETAILED DESCRIPTION

Embodiments of the present invention are directed to a cochlear implant electrode arrangement that resists post-surgical retraction of the inserted electrode array back out of the electrode opening due to growth of the mastoid bone. Such arrangements also avoid pressing excess slack in the electrode lead against an anatomical structure such as the skin covering skull bone behind the ear or covering the outer ear canal.

Figure 1:
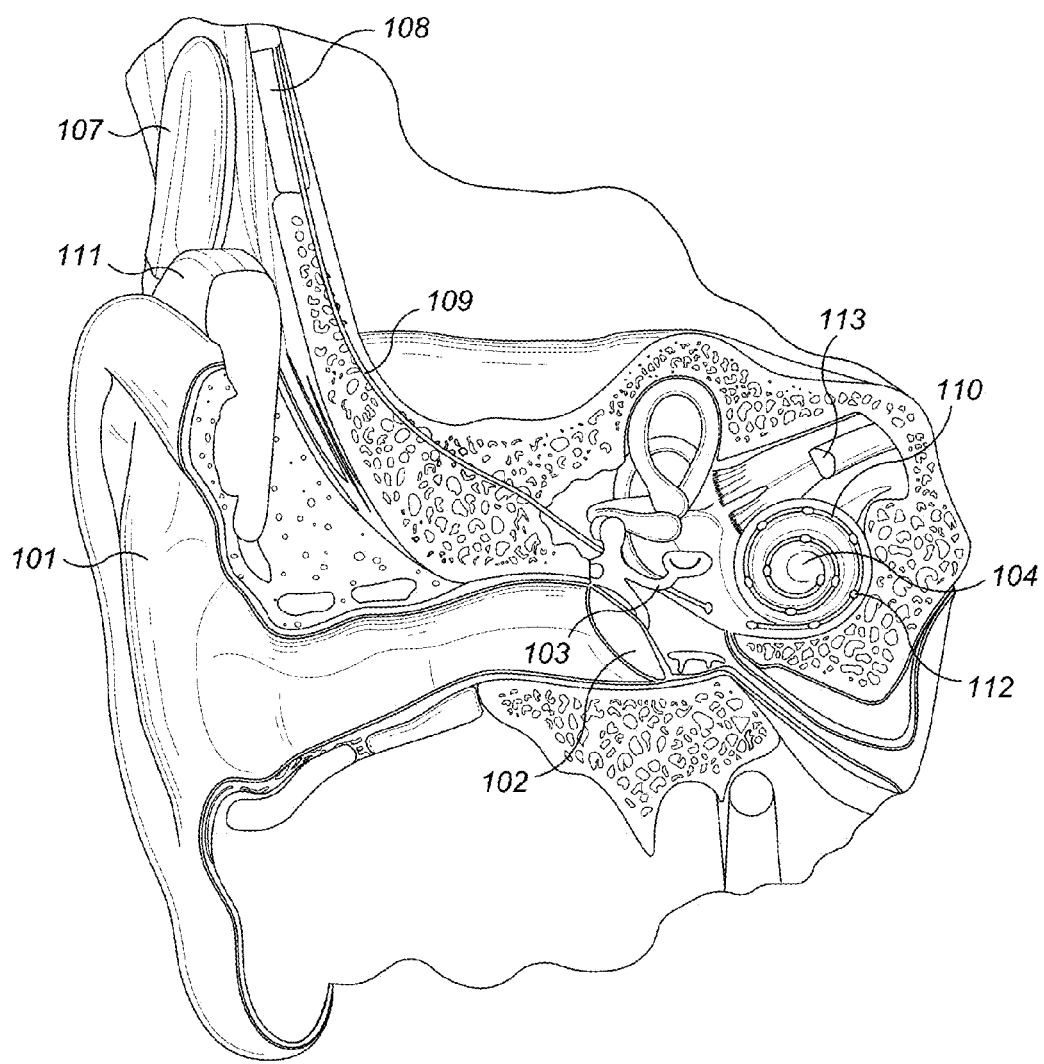
FIG. 1 shows various anatomical structures in a human ear and some components of a typical cochlear implant system.
Figure 2A:
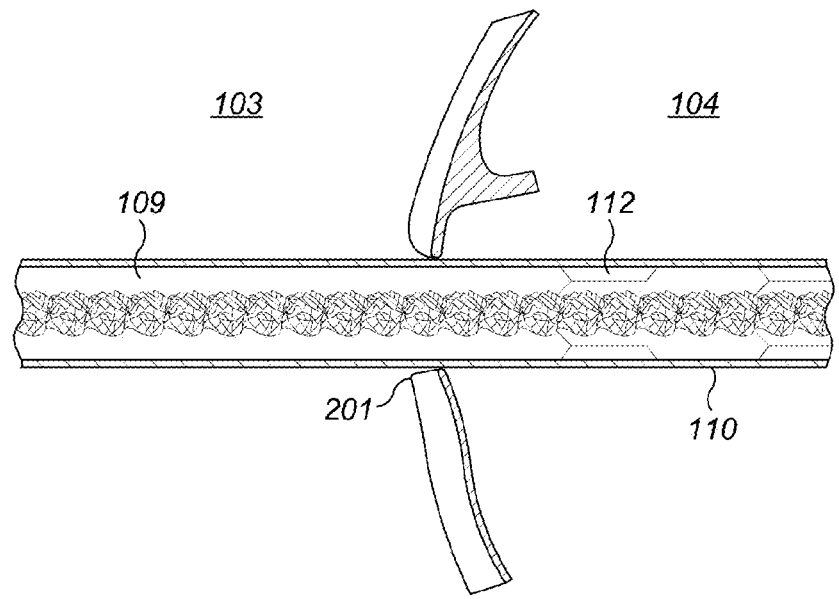
FIG. 2A shows structural details of a cochlear implant electrode arrangement at the electrode opening into the implanted cochlea.
Figure 2B:
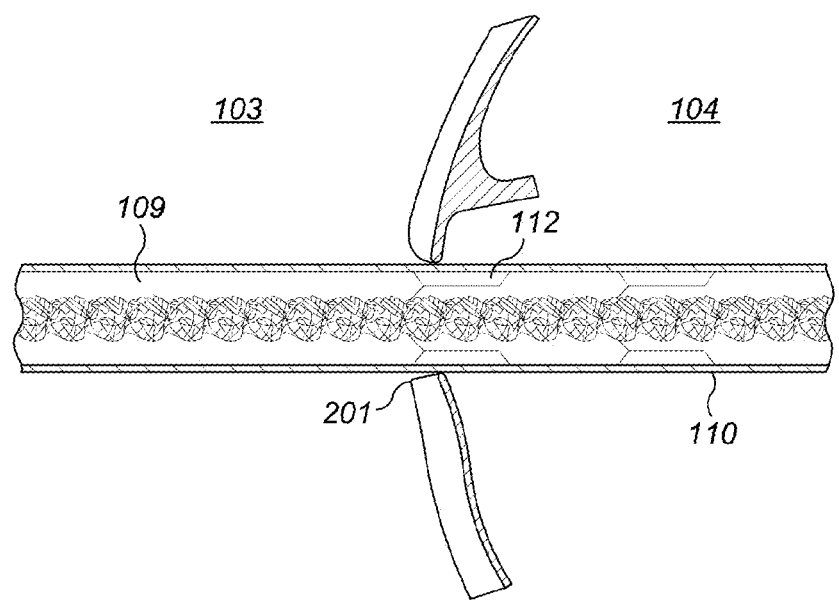
FIG. 2B shows how the proximal end of the intracochlear electrode array can retract back out of the electrode opening to pull the nearest electrode contact back into the electrode opening.
Figure 3A:
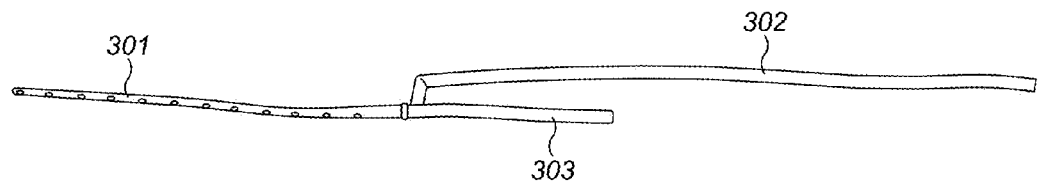
FIGS. 3A-3B show an electrode arrangement according to an embodiment of the present invention with a malleable lead holder.
Figure 3B:
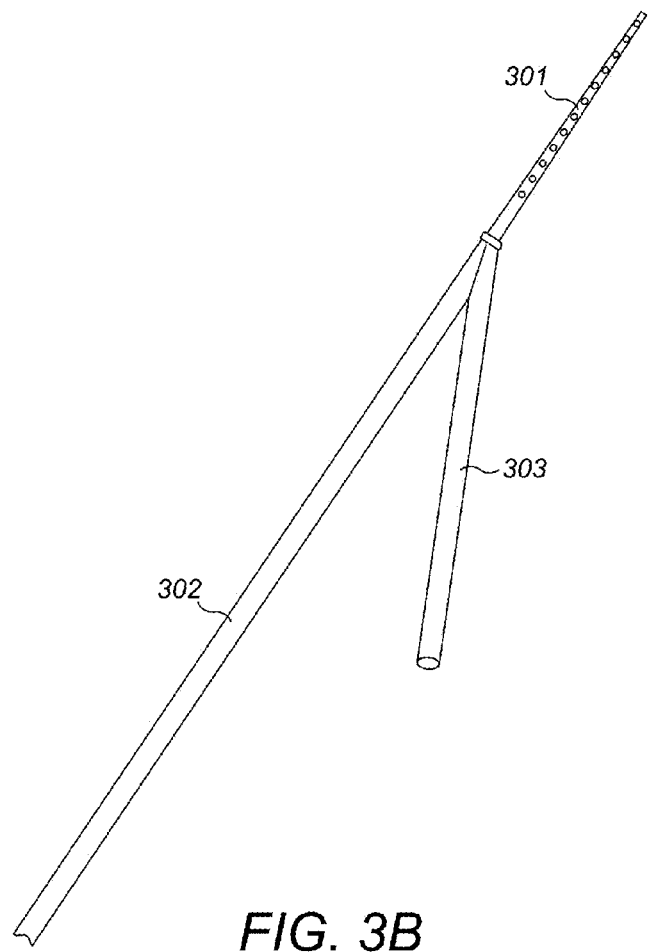

One such arrangement for an implantable electrode of a cochlear implant system uses a malleable lead holder structure as shown in FIGS. 3A-3B. A flexible intracochlear electrode array 301 has an outer surface along which are distributed electrode contacts for applying cochlear stimulation signals to target neural tissue within the implanted cochlea. A flexible extracochlear electrode lead 302 is coupled at a lead proximal end coupled to an implanted signal processor that provides the cochlear stimulation signals. A lead distal end of the electrode lead 302 is coupled to a proximal end of the electrode array 301. A lead holder 303 is connected to the distal end of the electrode lead 302 and has an initial shape. The lead holder 303 is malleable and adapted to be intra-surgically deformed into and retain a new desired shape so as to secure the distal end of the electrode lead 302 at the electrode opening into the implanted cochlea so as to decouple post-surgical mechanical strain at the distal end of the electrode lead 302 (e.g., due to growth of the mastoid bone) from the electrode array 301.

In the specific embodiment shown in FIG. 3A, the lead holder 303 is in line with and extends out oppositely from the electrode array 301. The electrode lead 302 extends out from the lead holder 303 at a sharp perpendicular angle. The electrode lead 302 then has a second sharp bend after the perpendicular angle so that the electrode lead 302 extends substantially parallel to the electrode array 301, with a space of about 1-5 mm between them. FIG. 3B shows another embodiment where the electrode lead 302 is in line with the electrode array 301 as in a conventional implant electrode, and the lead holder 303 extends out at an angle from the distal end of the electrode lead 302. In both cases the length of the lead holder 303 typically may be between 2-7 cm, preferably around 3 cm. In particular the length of the lead holder 303 should match the dimensions of the mastoid bowl, and if that is enlarged during implantation surgery, the length of the lead holder 303 needs to correspond to the dimensions of the enlarged bowl.

The lead holder 303 may include one or more embedded nitinol wires with encapsulated in silicone. A portion of such a nitinol wire may extend into either or both of the electrode array 301 and/or the electrode lead 302. The nitinol wire may be isolated from the electrically conductive wires that connect to the electrode contacts in the electrode array 301. The point where the lead holder 303 branches off from the electrode lead 302 typically is at or slightly behind the electrode opening into the inner ear, i.e. at the round window, oval window, or any electrode opening caused by a cochleostomy.

Figure 4A:
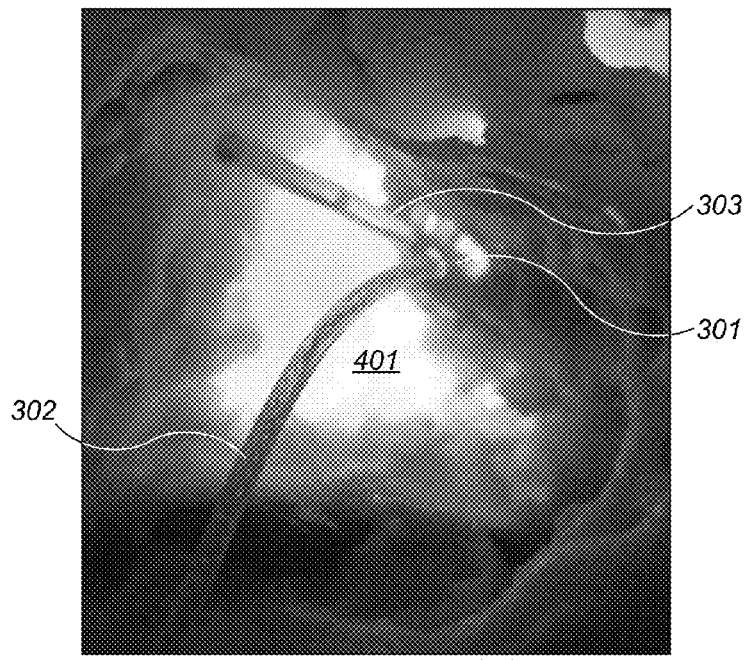
FIGS. 4A-4B show insertion of an electrode array into an implanted cochlea using a lead holder as shown in FIGS. 3A-3B.
Figure 4B:
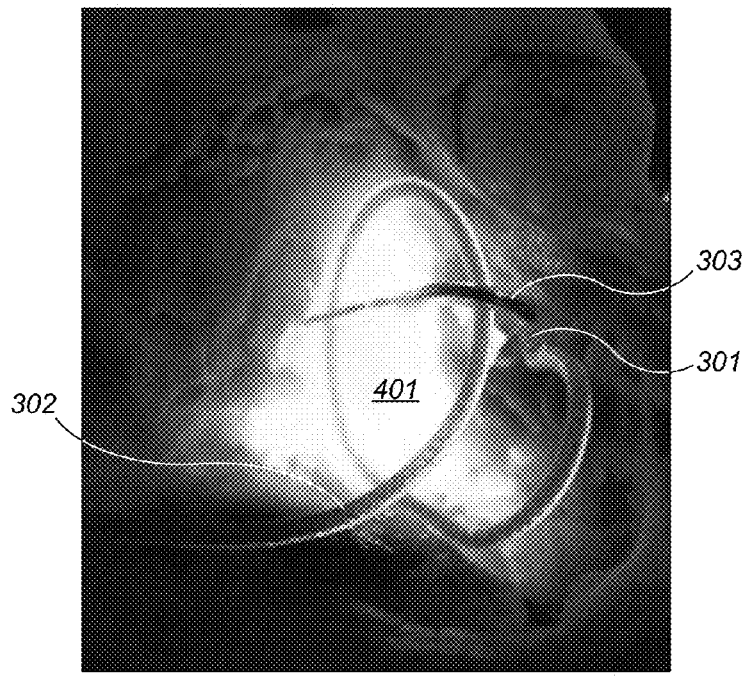

During insertion surgery, the surgeon may grip the holder element 303 instead of the electrode lead 302 if this is convenient. As shown in FIG. 4A-4B, after insertion of the electrode array 301 into the cochlea, excess electrode lead 302 may be positioned in the mastoid bowl 401 to account for later bone growth; for example, by forming loops or wavy shapes within the opening of the mastoid bowl 401. The free end of the holder element 303 may then be secured in bone or cartilage tissue of the mastoid bowl 401 approximately opposite the round window/oval window to hold in place the excess electrode lead 302. Since the lead holder 303 is malleable, it does not exert pressure in towards the implanted electrode array 301, but because of its stiffness, it also prevents the electrode array 301 from retracting back out of the electrode opening. Securing the excess electrode lead 302 in the mastoid bowl 401 with the lead holder 303 also avoids having the excess electrode lead 302 pressing against any adjacent soft anatomical structure such as the overlying skin. At the same time, if the mastoid bone of the patient grows after the implantation surgery, the excess electrode lead 302 stored in the mastoid bowl 401, can still expand out to account for the growth because the loops are just positioned within the mastoid bowl 401 by the lead holder 303, but they not fixed to anatomical structures therein.

Embodiments of the present invention also include an implantable electrode arrangement for a cochlear implant system without a malleable lead holder. For example, as shown in FIGS. 5A-5D, there is a flexible intracochlear electrode array 501 with electrode contacts for applying cochlear stimulation signals to target neural tissue within the implanted cochlea. A flexible extracochlear electrode lead 502 is coupled at a lead proximal end coupled to an implanted signal processor that provides the cochlear stimulation signals, and connected at a lead distal end to a proximal end of the electrode array 501.

The outer surface of the electrode lead 502 has string connectors 503 that are distributed thereon. In the specific embodiment shown in FIG. 5A-5D, the string connectors 503 are connector rings that protrude from the outer surface of the electrode lead 502. In other embodiments, the string connectors 503 may take other specific structural forms such as connector loops, etc. There are one or more connecting strings are attached at each end to a string connector 503 to form a string connection that holds together a loop of the electrode lead 502 between the attached string connectors 503. The loops are longer than the corresponding string connections, and in the specific embodiment shown in FIGS. 5B-5C, there initially are multiple such string connections that form electrode lead loops, either in pairs of string connections as in 505 and 506, or as individual string connections as in 504, 507, 508 and 509.

The string connections are adapted to be removed after healing of the implanted cochlea following insertion of the electrode array 501 into the cochlea to thereby decouple post-surgical mechanical strain on the electrode lead 501 from the electrode array 502. For example, the string connections may be adapted to be made of a biodegradable polymer string (and/or or the attached string connectors 503) that dissolves over time. In addition or alternatively, the connecting string and/or the attached string connectors 503 may be intended to be surgically cut to be removed. The removal over time of the string connections should be coordinated with mastoid bone growth in a young patient to compensate for that bone growth; for example, the thickness of the connecting string can be adjusted to control how long after surgery it takes for the connecting string to dissolve.

In the embodiment shown in FIGS. 5A-5D, the electrode arrangement includes a lead handling member 511 that projects out from the electrode lead 502 without conducting elements that carry the cochlear stimulation signals. The lead handling member 511 may include an embedded malleable core having an initial shape adapted to be intra-surgically deformed into and retain a new desired shape such as discussed above. For example, the embedded malleable core may include a nitinol element with malleable characteristics, etc.

Figure 5C:
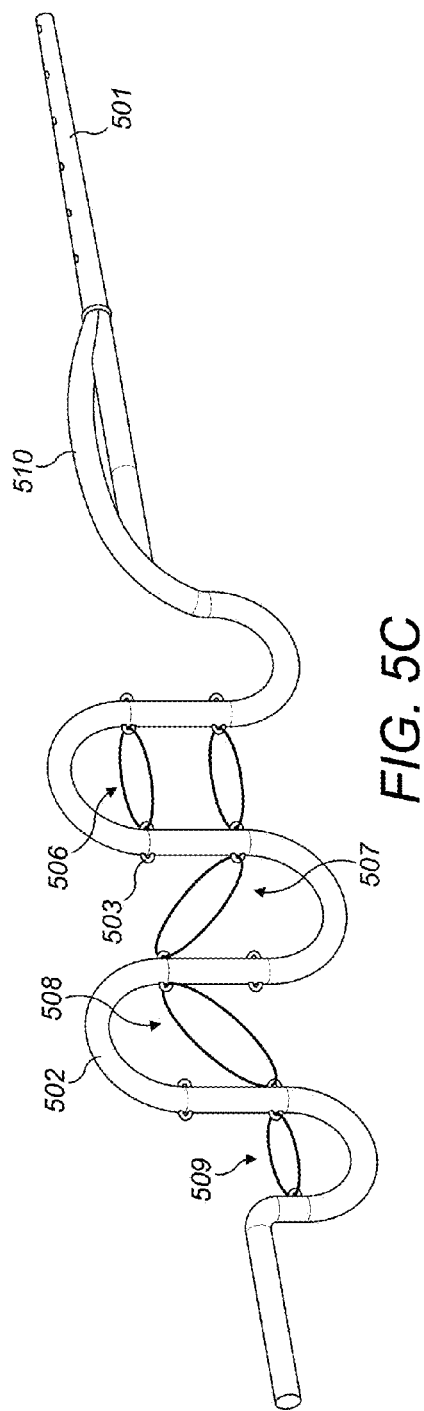
Figure 5D:
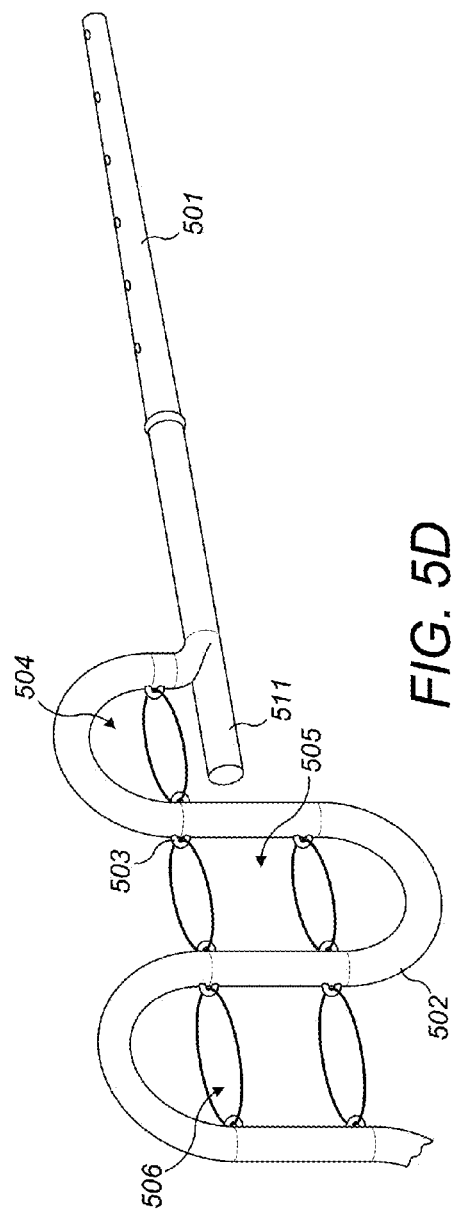
Figure 6A:
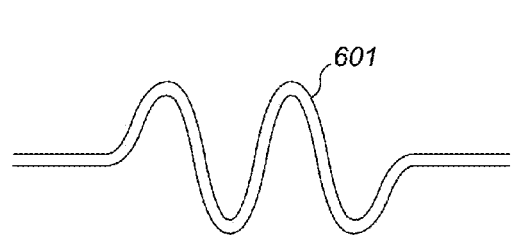
FIGS. 6A-6D show pre-shaped growth segment shapes for portions of electrode leads according to an embodiment of the present invention.
Figure 6B:
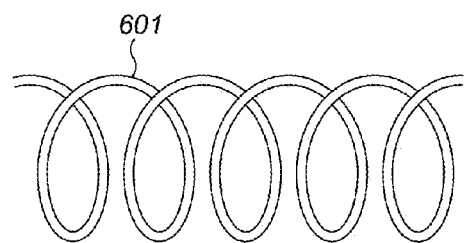
Figure 6C:
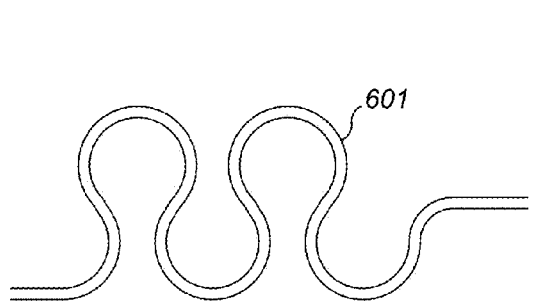
Figure 6D:
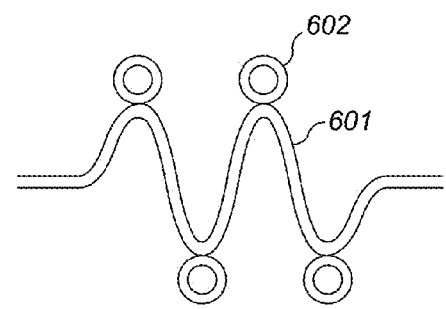

Prior to implantation, the electrode lead 502 may be configured with one or more string connections to form loops as shown in FIG. 5B. During surgical implantation, the receiver stimulator would be fixed in place first, and then the electrode lead 502 would be extended up to the electrode opening in the outer surface of the cochlea. If the length of the electrode lead 502 is then too short, then one of the string connections can be cut; for example, as shown in FIG. 5C where string connections 504 and 505 have been cut. That will allow the electrode lead 502 to extend further until it reaches the electrode opening.

Embodiments such as the one shown in FIG. 5A-5D are straightforward and uniform to implement so as to decouple post-surgical mechanical strain on the electrode lead 501 from the electrode array 502 without needing to loop excess electrode lead 501 in the mastoid opening.

Embodiments of the present invention also include electrode arrangements that are based on pre-formed, non-malleable electrode lead structures. For example, FIGS. 6A-6D show pre-shaped growth segment shapes 601 for portions of electrode leads that decouple post-surgical mechanical strain on the electrode lead from the electrode array. The sine-wave, helical shape and curved loop growth segment shapes 601 depicted in FIGS. 6A-6C respectively all allow account for mastoid bone growth by allowing straightening of the electrode lead. And as in the embodiments shown in FIGS. 5A-5D, any of the growth segment shapes 601 may also incorporate string connectors 602 that allow use of string connections that may dissolve over time after surgery. The growth segment shapes 601 may be incorporated into the electrode lead anywhere along its length, whether closer to the implanted stimulator or to the electrode opening into the cochlear surface. Again one advantage of such arrangements it avoidance of the need to loop excess electrode lead in the mastoid opening.

As shown in FIGS. 7A-7G, specific electrode arrangements with stress decoupling growth segments such as the ones shown in FIGS. 6A-6D may also add circular or semi-circular flexible lead fixation rings through which the electrode lead can be looped. For example, in the embodiment shown in FIG. 7A, electrode lead 702 is connected at its proximal (or base) end to an implanted stimulator 701 that generations the electrode stimulation signals for the electrode array 703 at the distal (or apical) end of the electrode lead 702. Near the implanted stimulator 701, the electrode lead 702 includes a sine wave growth segment 705 with a semi-circular lead fixation ring 704 in parallel. The electrode stimulation signals pass along wires embedded in the electrode lead 702 including the growth segment 704, but not through the lead fixation ring 704 which is a structure that the more apical/distal portions of the electrode lead may be looped through to have enough excess electrode lead with slack so as to accommodate post-surgical mastoid bone growth.

Figure 7A:
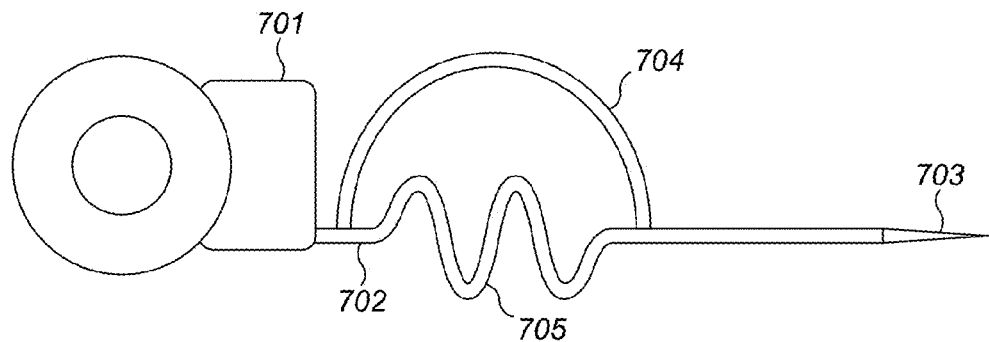
FIGS. 7A-7G show an electrode arrangement according to an embodiment of the present invention with pre-shaped growth segments.
Figure 7B:
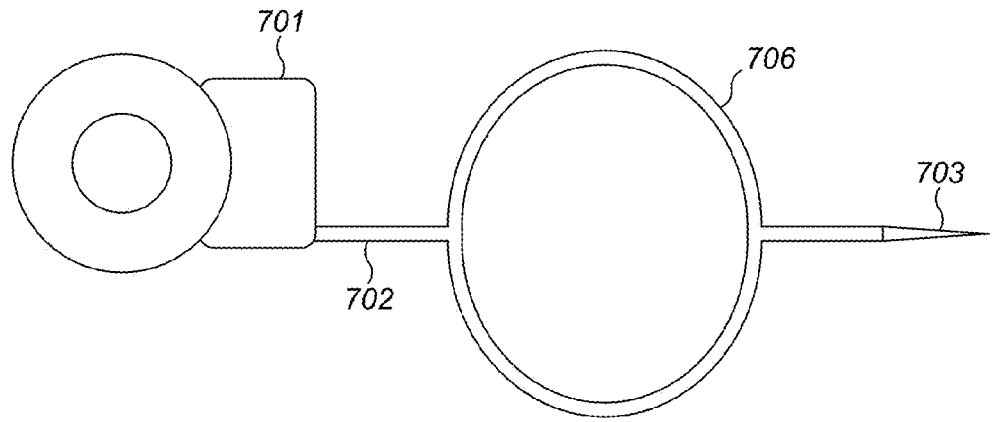
Figure 7C:
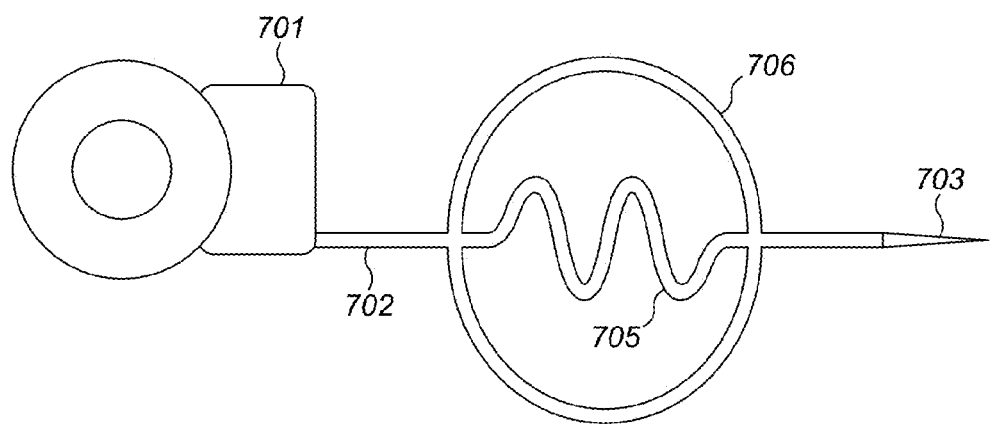
Figure 7D:
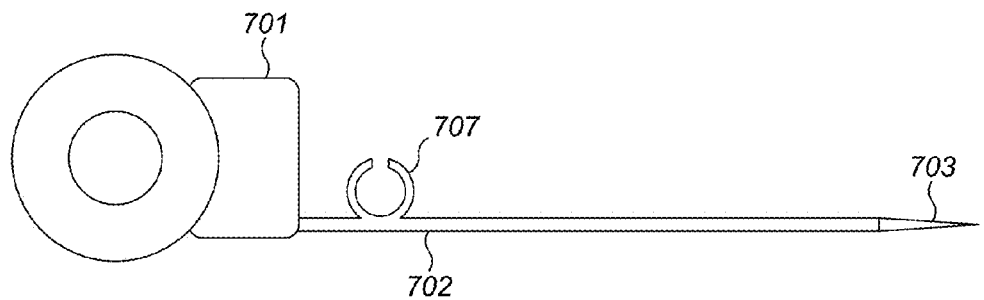
Figure 7E:
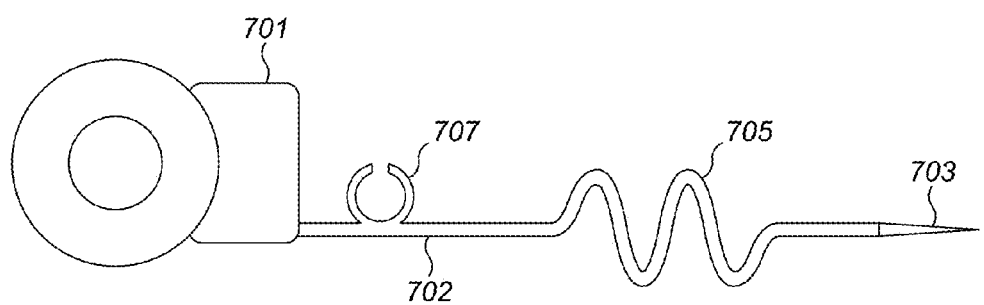
Figure 7F:
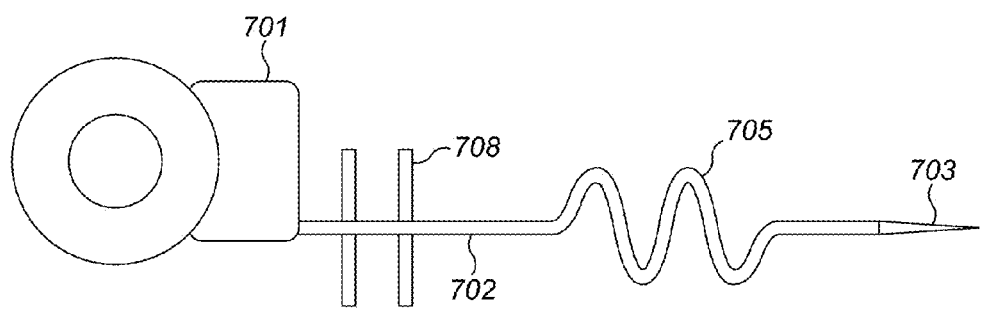
Figure 7G:
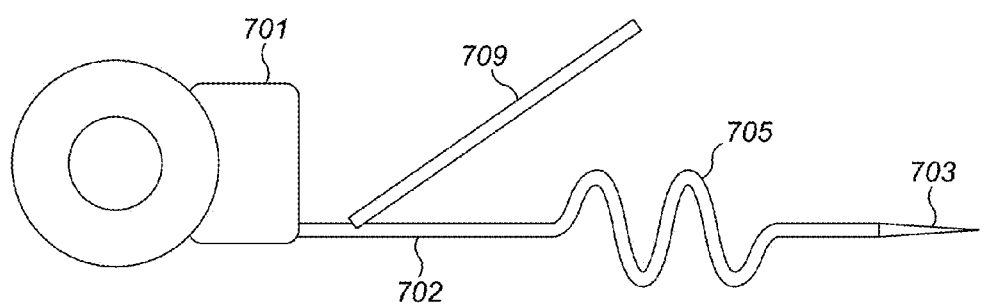

In the embodiment shown in FIG. 7B. the circular lead fixation ring 706 is part of the electrode lead 702 in that one or both loops of the lead fixation ring 706 contain electrode wires that carry the electrical stimulation signals from the implanted stimulator 701 to the electrode array 703. The electrode arrangement shown in FIG. 7C combines a sine wave shape growth segment 705 that includes the electrode wires, with a non-wired circular lead fixation ring 706. The embodiments shown in FIGS. 7D and 7E have a smaller lead fixation ring 707 with a split opening through which the electrode lead 702 can be looped. FIGS. 7F and 7G show embodiments of an electrode arrangement having malleable projections 708 and 709 that can be deformed over or around adjacent bone/tissue. Lead fixation ring 707 and malleable projections 708 and 709 may be movable along electrode lead 702.

Figure 8:
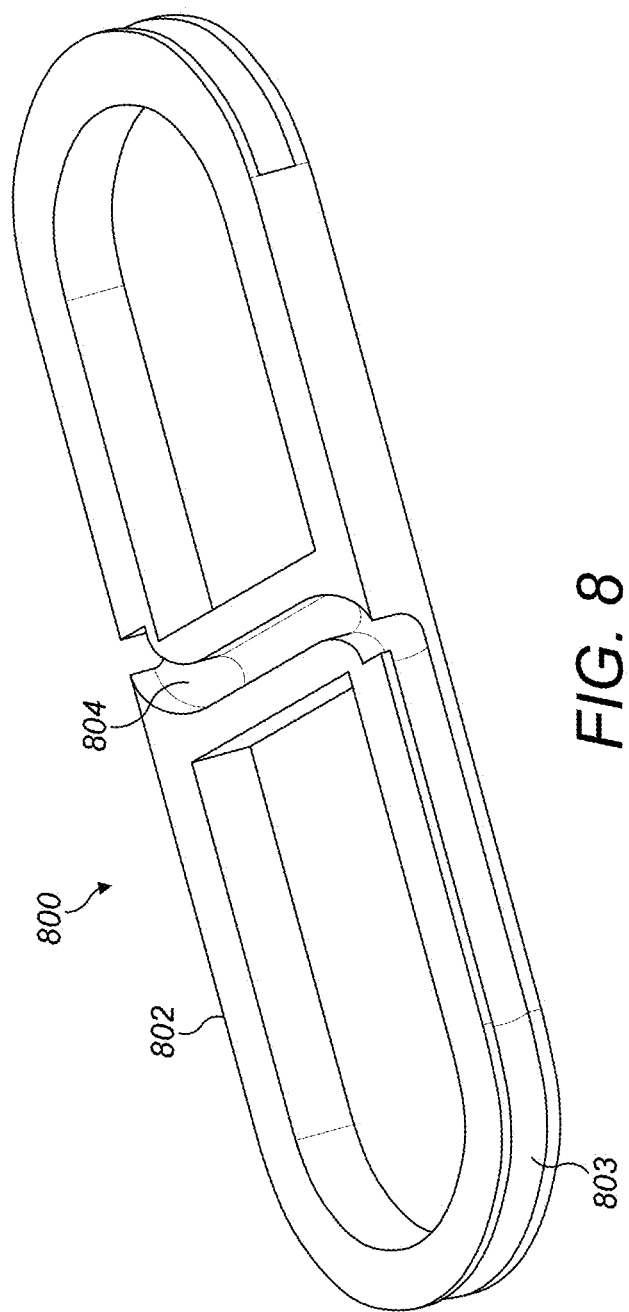
FIG. 8 shows an example of a lead deforming tool according to an embodiment of the present invention.

FIG. 8 shows an example of a lead deforming tool 800 on which the electrode lead can be bent and fixed. The snapping tool 800 has a figure-eight shaped lead support 802 with an outer groove 803 around its outer circumference, and an inner groove 804 across its center. The electrode lead can be wound around the tool 800 to form loops as required.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable electrode arrangement for a cochlear implant system, the arrangement comprising:
    a flexible intracochlear electrode array configured for insertion into the implanted cochlea, the electrode array having:
        i. an array proximal end configured for passing through an electrode opening in the outer surface of an implanted cochlea,
        ii. an array distal end terminating within the implanted cochlea, and
        iii. an outer surface with a plurality of electrode contacts configured for applying cochlear stimulation signals to target neural tissue within the implanted cochlea; and
    a flexible extracochlear electrode lead configured for carrying the cochlear stimulation signals, the electrode lead having:
        i. a lead proximal end coupled to an implanted signal processor that provides the cochlear stimulation signals,
        ii. a lead distal end connected to the array proximal end at the electrode opening,
        iii. an outer surface having a plurality of string connectors distributed thereon, and
        iv. at least one connecting string attached at each end to a string connector to form a string connection that holds together a loop of the electrode lead between the attached string connectors, the loop being longer than the string connection;
    wherein the string connection is adapted to be removed after healing of the implanted cochlea following insertion of the electrode array to thereby decouple post-surgical mechanical strain on the electrode lead from the electrode array.

2. The electrode arrangement according to claim 1, wherein the string connectors are connector rings protruding from the outer surface.

3. The electrode arrangement according to claim 1, wherein the string connectors are connector loops attached to the outer surface.

4. The electrode arrangement according to claim 1, wherein the string connection is adapted to be removed by biodegrading over time of the connecting string or the attached string connectors.

5. The electrode arrangement according to claim 1, wherein the string connection is adapted to be removed by surgical cutting of the connecting string or the attached string connectors.

6. The electrode arrangement according to claim 1, further comprising:
    a lead handling member projecting out from the electrode lead without conducting elements that carry the cochlear stimulation signals.

7. The electrode arrangement according to claim 6, wherein the lead handling member includes an embedded malleable core having an initial shape adapted to be intra-surgically deformed into and retain a new desired shape.

8. The electrode arrangement according to claim 7, wherein the embedded malleable core includes a nitinol element with malleable characteristics.

9. A cochlear implant system having an electrode arrangement according to any of claims 1-8.

* * * * *